United States Patent [19]

Schaeffer et al.

[11] Patent Number: 4,665,022
[45] Date of Patent: May 12, 1987

[54] BIOLUMINESCENT ASSAY REAGENT AND METHOD

[75] Inventors: James M. Schaeffer; Aaron J. Hsueh, both of San Diego, Calif.

[73] Assignee: The Regents of the University of California, Berkeley, Calif.

[21] Appl. No.: 581,242

[22] Filed: Feb. 17, 1984

[51] Int. Cl.[4] .................. G01N 33/53; G01N 33/566; G01N 33/536; G01N 33/532
[52] U.S. Cl. ..................................... 435/7; 436/501; 436/536; 436/544; 436/547; 436/172; 435/8; 530/802
[58] Field of Search ............... 436/536, 537, 501, 543, 436/544, 819, 547, 172; 435/7, 8; 260/112 R; 534/756, 764, 822, 824; 530/802

[56] References Cited
U.S. PATENT DOCUMENTS 4,104,029 8/1978 Maier, Jr. .................................. 435/7
4,232,119 11/1980 Carlsson et al. ......................... 435/7

OTHER PUBLICATIONS

White, E. H. et al., (1965) J. Org. Chem. 30:2344–2348.

Primary Examiner—Sidney Marantz
Assistant Examiner—Jack Spiegel
Attorney, Agent, or Firm—Brown, Martin, Haller, & Meador

[57] ABSTRACT

Reagent for immunoassay, ligand binding assay and ligand receptor assay in which luciferin is covalently bonded to a molecule having biological activity for bonding to a particular biologically active group of a material and method in which the luciferin and biologically active molecule conjugate is added to a material having a group for combination with the biological activity of the conjugated molecule, the mixture is incubated to bond the material to the reagent through the biological activity and the product of the bonding is reacted with luciferase to produce bioluminescence having intensity dependent on the concentration of the material being assayed.

4 Claims, 6 Drawing Figures

BIOLUMINESCENT ASSAY REAGENT AND METHOD

FIELD OF THE INVENTION

This invention relates to bioluminescent reagents and methods for immunoassays, ligand binding asay or ligand receptor assays.

BACKGROUND OF THE INVENTION

Radio-immunoassays and radio-receptor assays using radiolabeled tracers are widely used for the specific quantitation of small amounts of antigens or receptors respectively in biological fluids. However, the sensitivity of these assays is limited by the specific activity of the radio-isotope; and, for example in studies of nicotinic acetylcholine (nACh) receptors in brain, this presents a problem due to the relatively low tissue concentration. Additionally, use of radioactive material presents serious problems in storage, handling and disposal.

Non-radioisotopic probes have been developed for use in immunoassays by conjugating antigens to compounds with fluorescent or chemiluminescent properties as well as to free radicals and enzymes. However, sensitivity of these immunoassays is generally not superior to the classical radioimmunoassays.

Bioluminescent immunoassays have been developed in which the ligand is covalently linked to firefly luciferase. Although the reported sensitivity of these bioluminescent assays is comparable to radioimmunoassays, and the theoretical sensitivity is greater due to the sensitivity of the luciferin-luciferase reaction, luciferase is somewhat unstable and is subject to degradation by proteolytic enzymes. Also, the luciferase molecule is relatively large and may introduce steric changes in the ligand to be studied.

BRIEF SUMMARY OF THE INVENTION

It is an object of the present invention to provide a stable highly sensitive bioluminescent assay reagent based on luciferin activity and an assay method using that reagent which avoids both the handling, storage and disposal problems of radioactive labeled reagents and the stability, steric and other difficulties of previous bioluminescent assay reagents and methods.

BRIEF DESCRIPTION OF THE DRAWINGS

Reference is made to the drawings forming part of the present disclosure. In the drawings.

DETAILED DISCLOSURE OF THE INVENTION

Figure 1:
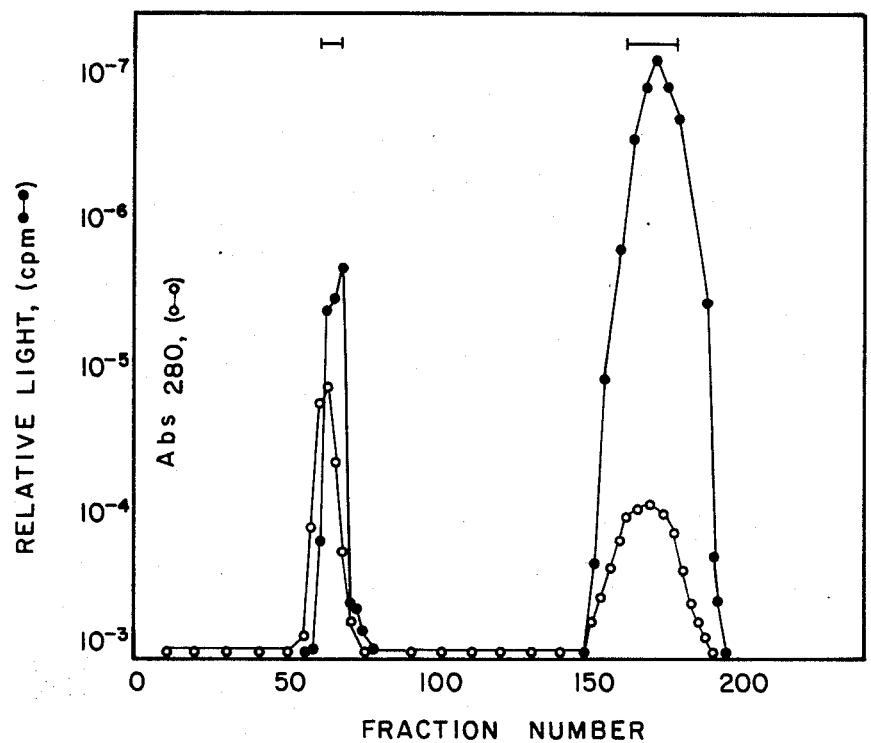
FIG. 1 shows the elution profile of the reaction mixture containing alpha-bungarotoxin and luciferin off a Sephadex G 75 column. The products resulting from the reaction were identified by monitoring the absorption of the fraction at 280 nm (o—o), and assaying for luciferin dependent light emission in the presence of excess luciferase and ATP (o—o)

The immunoassay, ligand binding assay and ligand receptor assay reagents of the present invention are a combination of a luciferin-label component capable of extremely sensitive quantitative measurement covalently joined with a molecule having biological activity for bonding to a particular biologically active group of a material.

Biologically active components to which a luciferin label may be joined include steroids such as estradiol, testosterone and progesterone; polypeptides, such as releasing factors, e.g. gonadotropin releasing factor, or growth hormone releasing factor, insulin, prolactin, alpha-bungarotoxin, Protein A, avidin, immunoglobins, and thyroid stimulating hormone; nucleotides particularly cyclic nucleotides such as cyclic adenosine monophosphate and cyclic guanosine monophosphate, nitrogenous bases such as naloxone and digoxin; and neurotransmitters such as dopamine· alpha-amino-butyric acid and acetylcholine.

These components possess or may be modified to possess active hydroxyl, amino or carboxyl groups by means of which a luciferin label may be covalently attached which retaining both the biological activity of the component and the bioluminescent ability of the luciferin label, i.e. the ability to produce photons of light in the presence of luciferase, magnesium and adenosine triphosphate.

Two procedures have been developed for covalent linkage of luciferin to biologically active molecules. In some cases it has been possible covalently to link luciferin to biologically active molecules, such as polypeptides, e.g. alpha-bungarotoxin, as shown in the following equations to form by condensation through the action of a carbodiimide a covalently joined luciferin label and biologically active moiety:

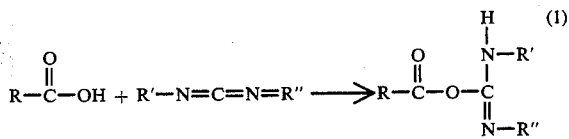

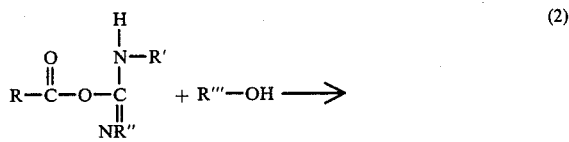

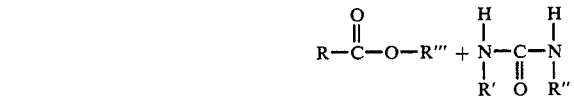

In equations (1) and (2), R' and R" may be the same or different and may be hydrogen or aliphatic or aromatic groups; R is a biologically active group having or being modified to have a reactive hydroxyl, amino or carboxyl group; and R'"—OH is luciferin.

In the above reaction it is preferred to use relatively low molecular weight carbodiimides such as N,N'-diisopropyl-carbodiimide.

The resulting product, alpha-bungarotoxin-luciferin was purified by column chromatography and demonstrated to have both alpha-bungarotoxin and luciferin activity.

In another procedure, an amino-terminated luciferin derivative which retains luciferin activity is prepared by the following reaction:

-continued 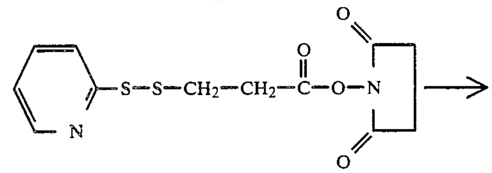 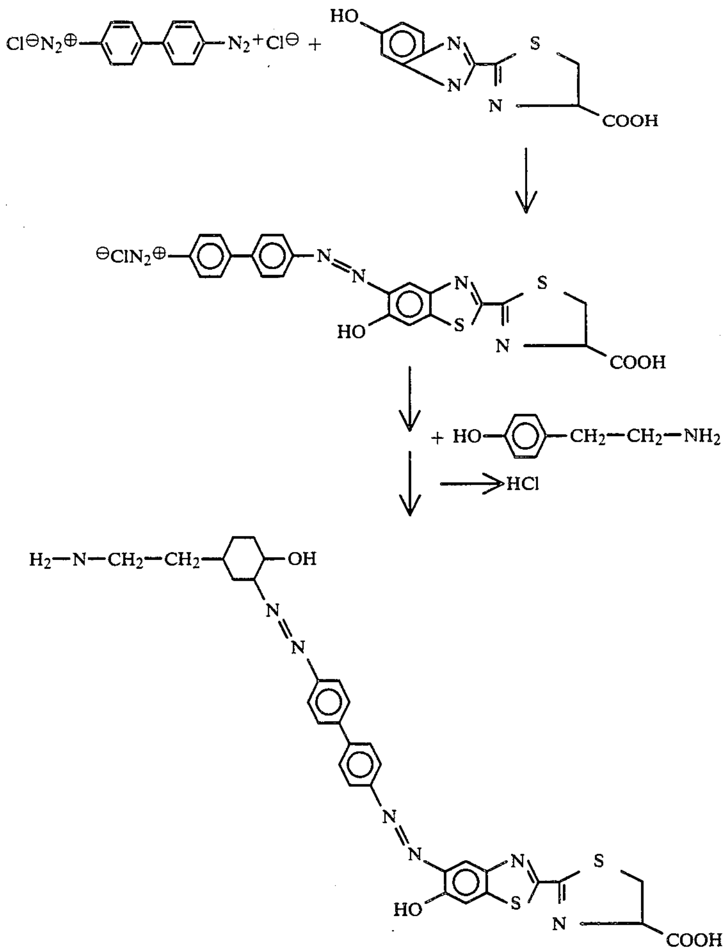 equation #3 equation #4

In equations (3) above, bis-diazotized benzidine is reacted with firefly luciferin and in equation (4), the reaction product from equation (3) is reacted with tyramine to form a luciferin derivative having a terminal $-NH_2$ group.

The resulting amino-terminated luciferin may be covalently bonded to a biologically active component through an initial reaction of the luciferin compound with N-succinimidyl-3-(2-pyridyldithio)propionate, (SPDP), to form luciferin-SPDP. Since SPDP is a heterobifunctional reagent, the luciferin-SPDP readily forms covalent links to biological molecules such as protein, peptides, and steroids as shown in the following equations:

Ⓛ $-NH_2$ + (5)

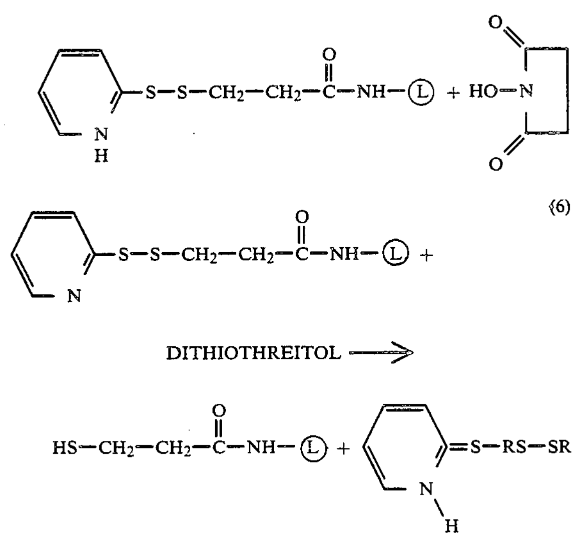

(6)

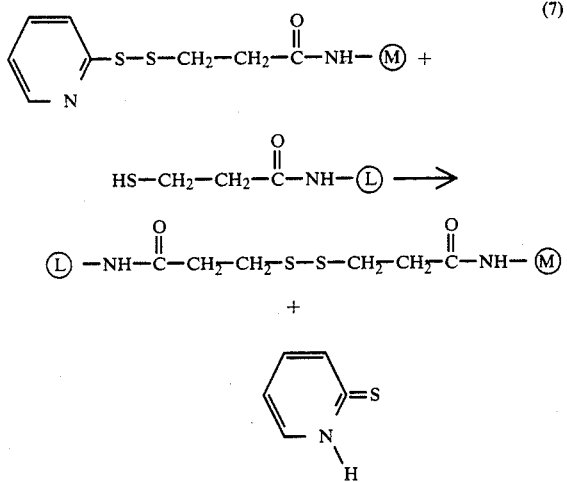

In equations (5), (6) and (7) ⓛ —NH₂, is the amine terminated luciferin reaction product resulting from reaction (4) and Ⓜ is a biologically active group.

Equation (5) shows introduction of 2-pyridyl disulfide to the amine-terminated luciferin reaction product by reaction with SPDP. Equation (6) shows the thiolation of the product of equation (5) by addition of dithiothreitol to form a modified product retaining luciferin activity and equation (7) shows covalent linkage of the product of introduction of 2-pyridyl disulfide to a biologically active group by combination with SPDP with the modified luciferin product of equation (6) through a disulfide bond.

The purified luciferin-derivatized compounds are stable (at 4° C. for at least 30 days, or indefinitely when lyophilized) and will act as a substitute for $^{125}$I-labeled compounds for use in bioluminescent immunoassays or bioluminescent ligand receptor assays. The concentration of luciferin in these compounds is determined by adding a saturating concentration of luciferase and measuring the amount of light emitted using a standard liquid scintillation spectrophotometer. The amount of light emitted is proportional to the amount of luciferin present. As low as $10^{-17}$ moles of luciferin produces detectable amounts of light.

The presence of the luciferin moiety label attached to biologically active compounds has been found not to reduce significantly the biological activity of such compounds or their ability to combine with substantially all of the corresponding activity with which the unlabeled biologically active compounds would combine. Also, the luciferin label does not interfere with the binding specificity of the biologically active compounds.

The following examples are given to aid in understanding the invention but it is to be understood that the invention is not limited to the particular materials, procedures or other details of the examples.

Example 1

A solution was prepared containing 0.4 mg. of alpha-bungarotoxin and 25 mg. of diisopropyl carbodiimide in 0.25 ml. of Krebs' bicarbonate buffer (124 mM NaCl, 5 mM KCl, 26 mM NaHCO₃, 1.2 mM KH₂PO₄ and 1.3 mM MgSO₄, pH 7.4) containing 5% ethanol. The solution was incubated 22° C. for 15 minutes and then 0.25 mg. of firefly luciferin, a twenty-five-fold molar excess, dissolved in 0.25 ml. of distilled water was added to the solution and the incubation was continued for 18 hours at 22° C. The mixture was then placed on a Sephadex G-75 chromatographic column (1×20 cm.) and eluted with Krebs' bicarbonate buffer to separate alpha-bungarotoxin-luciferin from excess unbound luciferin and carbodiimide.

Two peaks were observed by measuring absorbance at 280 nm (FIG. 1). The first peak has an estimated molecular weight of 8000 daltons and comigrates with alpha-bungarotoxin, (alpha-BTX). The second peak is greatly retarded by the Sephadex G-75 and comigrates with synthetic firefly luciferin. The luciferin activity of each fraction was quantitated by measuring the amount of light produced in the presence of excess luciferase and ATP. Luciferin activity was present in both peaks I and II. Greater than 90% of the luciferin activity was recovered from the column, with 6% present in peak I and the remainder in peak II. The material from peak I was routinely used in subsequent binding assays.

Figure 2:
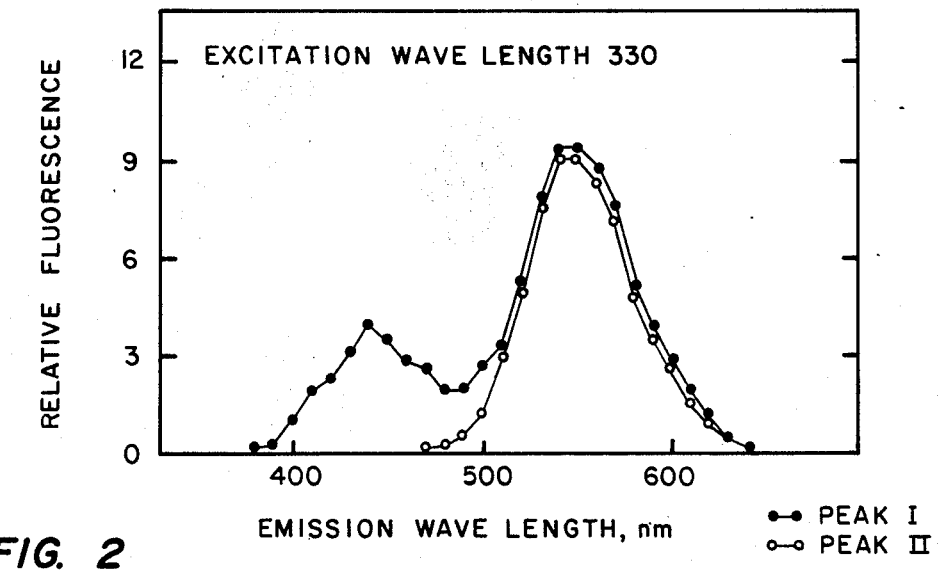
FIG. 2 is a graph comparing absorbance of luciferin and of the luciferin analog.

The fluorescence excitation and emission spectra of synthetic luciferin in peaks I and II were determined. Absorbance of radiation at wave lengths at 330 are shown in FIG. 2. The emission spectra for the material isolated in peak II is identical to authentic luciferin. Peak I has two maxima of emission at 440 and 550 nm. Alpha-bungarotoxin alone has no fluorescent properties. These results demonstrate that alpha-bungarotoxin-luciferin has an excitation spectra distinct from that of luciferin.

Determination of alpha-bungarotoxin-luciferin concentration—An estimate of the alpha-bungarotoxin-luciferin concentration was made by two series of receptor binding assays. Specific alpha-bungarotoxin-luciferin binding to cerebral cortical membranes was measured in the absence or presence of increasing concentrations of unlabeled alpha-bungarotoxin and the results were expressed as the ratio of the amount bound to the total alpha-bungarotoxin-luciferin present. A second set of experiments measured alpha-bungarotoxin-luciferin bound to cerebral cortex homogenates in the presence of increasing amounts of alpha-bungarotoxin-luciferin. The amount of specific binding was also expressed as the percent of alpha-bungarotoxin-luciferin bound. These experiments yield two parallel displacement curves which provide an estimate of the alpha-bungarotoxin-luciferin concentration.

A further portion of alpha-bungarotoxin was iodinated by means of the chloramine-T procedure. To 1 mCi of sodium [125I] iodide in 0.1 ml. of 0.1N dilute NaOH was added, sequentially, 0.1 ml of 0.5N sodium phosphate, pH 7.4, 0.04 mg. alpha-bungarotoxin in 0.1 ml. of H₂O, and 0.01 ml. of 25 mg/ml. chloramine-T. The reaction was stopped after 30 s by addition of 0.01 ml of 50 mg/ml. of sodium metabisulfite, and the mixture was immediately chromatographed on a Sephadex G-10 column to remove unreacted iodide. The iodinated alpha-bungarotoxin was further purified by gel chromatography with a carboxymethyl-cellulose column (1.0×50 cm).

Sprague-Dawley rats (175-200 g body weight) were used for all experiments. Rats were decapitated and tissue samples prepared by homogenization in Krebs' bicarbonate buffer (124 mM NaCl, 5 mM KCl, 26 mM NaHCO₃, 1.2 mM KH₂PO₄ and 1.3 mM MgSO₄, pH 7.4) at 4'C with a glass-glass homogenizer. Specific alpha-bungarotoxin-binding was measured by placing the homogenate (0.4 ml) into a 10×75 mm glass tube and incubating at 37° C. with alpha-bungarotoxin-luciferin in the presence (nonspecific binding) or absence (total binding) of a 500-fold molar excess of alpha-bungarotoxin. After 60 minutes the homogenate was transferred to microeppendorf tubes and washed two times with 1.5 ml. of ice-cold buffer by centrifugation for 5 minutes at 15,000 x g. The pellet was resuspended in 50 μl of Krebs' bicarbonate with a cell disrupter. In order to quantitate the amount of alpha-bungarotoxin-luciferin bound to the membranes, 20 μl of luciferase was added to the resuspended homogenate and placed immediately into a liquid scintillation spectrometer. The light emission was quantitated for 0.5 minutes.

Figure 3:
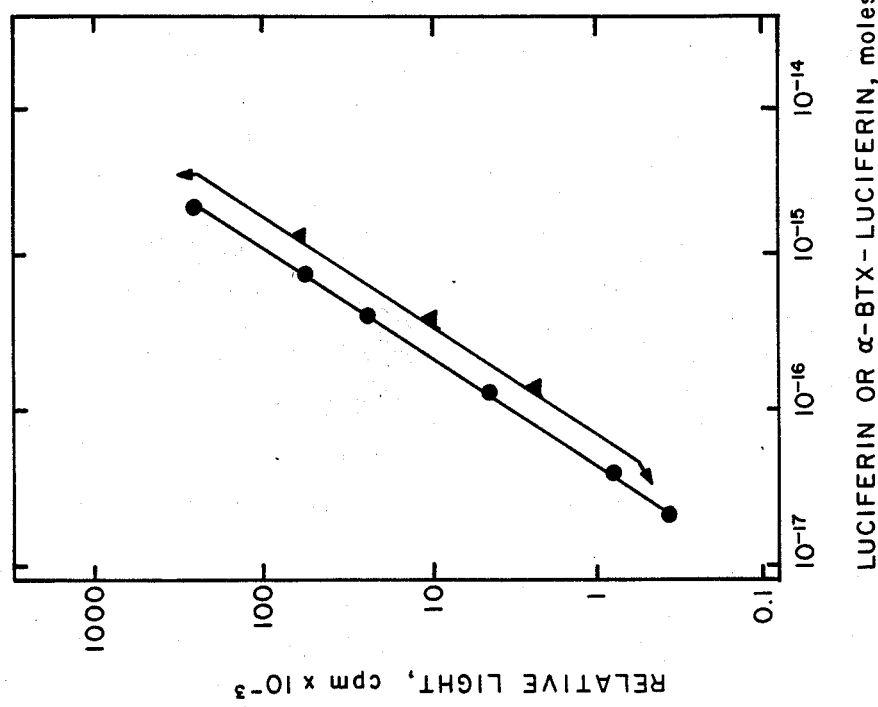
FIG. 3 shows the relative light emission of luciferin alone (o—o) and luciferin coupled to alpha-bungarotoxin (o—o) added.

As shown in FIG. 3, increasing amounts of luciferase added to a saturating concentration of luciferase and ATP result in a dose-dependent increase of light emission measured with a liquid scintillation spectrometer. The light emission increases proportionally with increasing concentrations of luciferin when expressed on a log-log scale over at least three orders of magnitude. As low as $3 \times 10^{-17}$ moles of luciferin produce detectable amounts of light. A parallel light emission curve is generated with increasing concentrations of alpha-bungarotoxin-luciferin (alpha-BTX-luciferin). The results (FIG. 4) indicate that there are 1.3 active molecules of luciferin/molecule of alpha-bungarotoxin. The limit of detectability of alpha-bungarotoxin-luciferin is $5 \times 10^{-17}$ moles (approximately 500 cpm).

Figure 4:
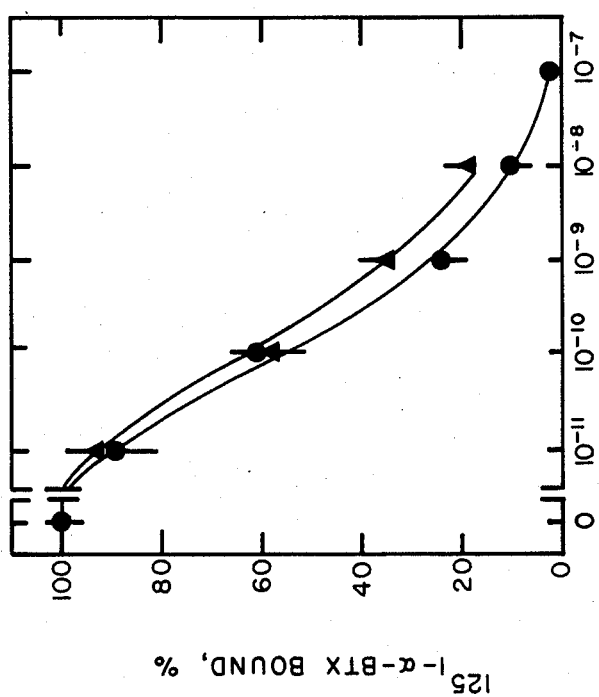
FIG. 4 is a graph comparing competition of alpha-bungarotoxin (Δ—Δ) and a luciferin analog of alpha-bungarotoxin (o—o) with $I^{125}$ labeled alpha-bungarotoxin.

The ability of luciferin conjugated alpha-bungarotoxin to bind nicotinic binding sites was examined by incubating membranes with 125I alpha-bungarotoxin with or without increasing concentrations of unlabeled alpha-bungarotoxin and alpha-bungarotoxin-luciferin. As shown in FIG. 4, unlabeled alpha-bungarotoxin displaces [125I] alpha-bungarotoxin and produces a parallel curve with a similar $K_I$ of 0.13 nM. These data demonstrate that the conjugation of luciferin to alpha-bungarotoxin does not significantly alter its ability to interact with nicotinic binding sites.

Figure 5:
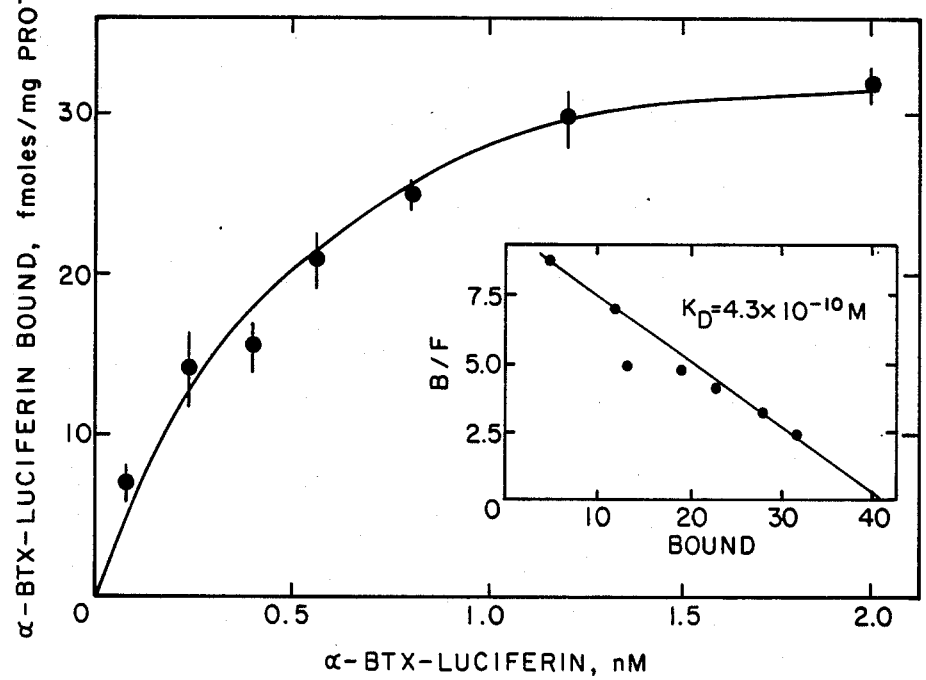
FIG. 5 is a graph showing the binding of a luciferin analog to rat cerebral cortex.

Nicotinic ACh receptors were studied in the central nervous system using the nonradiolabeled alpha-bungarotoxin-luciferin. Specific alpha-bungarotoxin-luciferin binding to membrane fractions from the cerebral cortex is saturable with increasing concentrations of alpha-bungarotoxin-luciferin (FIG. 5). The Scatchard analysis of these data yields a straight line, consistent with the existence of a single class of alpha-bungarotoxin-luciferin binding sites with high affinity ($K_D=0.43$ nM) and low capacity (42 fmol/mg protein). These results are consistent with previously reported data using $^{125}$I-alpha-BTX for receptor characterization.

Figure 6:
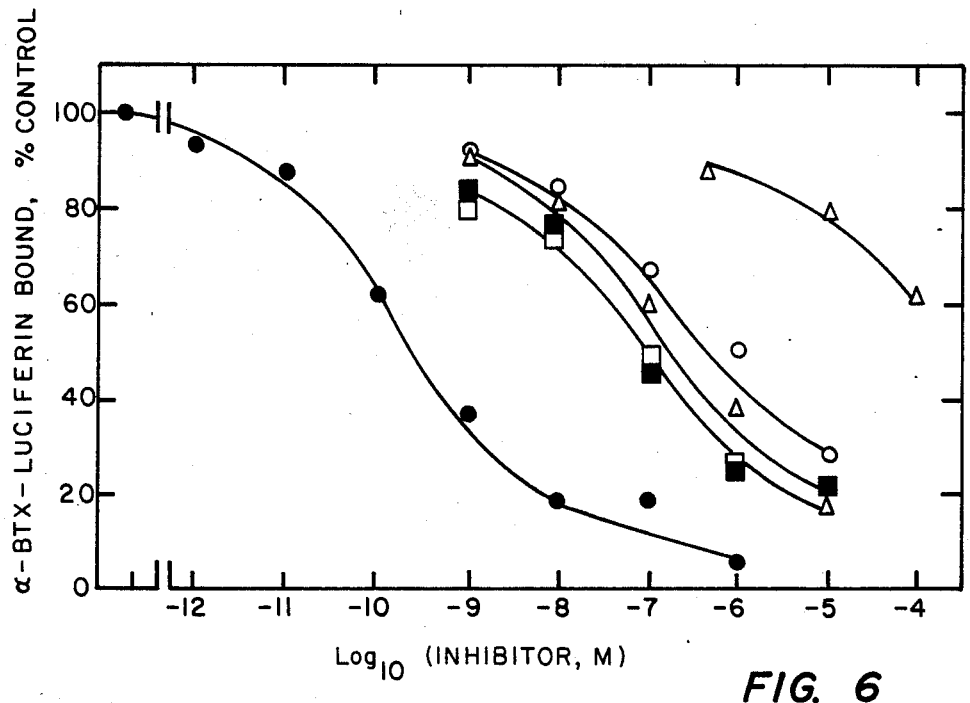
FIG. 6 is a graph showing competition of an alpha-bungarotoxin-luciferin to rat cerebral cortex by cholinergic agonists and antagonists; (▲—▲), scopolamine; (o—o), nicotine; (Δ—Δ), carbamyl choline; (■—■, lobeline; (□—□), d-tubocurarine.

To assess the specificity of alpha-bungarotoxin-luciferin binding to nACh receptors in the cerebral cortex, the ability of various compounds to displace alpha-BTX-luciferin was examined (FIG. 6). Alpha-bungarotoxin is the most potent inhibitor with a $K_I$ of 0.12 nM. Nicotine, carbamyl choline and lobeline (nicotinic agonists) and d-tubocurarine (a nicotinic antagonist) inhibit specific alpha-bungarotoxin-luciferin binding with $K_I$ values of 450, 200, 60 and 60 nM, respectively. In contrast, scopolamine, a potent muscarinic antagonist is much less effective ($K_I>10$ mM). These data demonstrate the specific interaction of alpha-bungarotoxin-luciferin with the nACh receptor. The sensitivity of this binding assay is determined by measuring specific alpha-bungarotoxin-luciferin binding to decreasing concentrations of cerebral cortex homogenate. The tissue is incubated in the presence of a near-saturating concentration of alpha-bungarotoxin-luciferin (2 nM), and amount of specific binding is linearly proportional to the amount of tissue from 5 to 400 μg protein (data not shown).

Specific alpha-bungarotoxin-luciferin binding was used to quantitate nACh receptors in various regions of the brain and peripheral tissues (see Table I). The highest concentrations of binding sites are detected in the hypothalamus and cerebral cortex. Three regions within the hypothalamus were also examined. High levels of alpha-bungarotoxin-luciferin binding sites are localized within the suprachiasmatic nucleus (91 fmol/mg protein) with lower concentrations in the supraoptic nucleus (30 fmol/mg protein) and median eminence (42 fmol/protein). Other brain regions and pituitary have lower, yet measurable levels of alpha-bungarotoxin-luciferin binding. In peripheral tissues examined, kidney has higher concentrations of nACh receptors than diaphragm, skeletal muscle and ovary (see Table I).

| Tissue | Specific binding of alpha-BTX-luciferin (fmol/mg protein) |
|---|---|
| Hypothalamus | 35 ± 4 |
| Suprachiasmatic nucleus | 91 ± 9 |
| Median eminence | 42 ± 6 |
| Supraoptic nucleus | 30 ± 9 |
| Cerebral cortex | 35 ± 1 |
| Anterior pituitary | 16 ± 4 |
| Pineal gland | 13 ± 0.4 |
| Posterior pituitary | 7 ± 3 |
| Cerebellar cortex | 4 ± 0.3 |
| Retina | 4 ± 0.1 |
| Kidney | 7 ± 1 |
| Ovary | 5 ± 1 |
| Skeletal muscle | 2 ± 1.4 |
| Diaphragm muscle | 1 ± 0.6 |

EXAMPLE 2

Firefly luciferin was covalently linked to gonadotropin-releasing hormone (GnRH) agonist, des-Gly[10]-D Glu[6]-Pro[9]-NHEt-GnRH using the procedure of Example 1, but using 1-cyclo-hexyl-3-(2-morpholino-ethyl-carbodiimide metho-p-toluene sulfonate rather than the diisopropyl carbodiimide of Example 1. The resulting GnRH A-luciferin conjugate was purified by passage through a Sephadex G-25 column followed by reverse thin layer chromatography. The purified material was found to have approximately the same bioactivity as GnRH and to compete with $^{125}$I buserelin (a GnRH agonist) for specific binding to the anterior pituitary.

The highest concentrations of GnRH A-luciferin binding sites were observed in the anterior pituitary (280 fmol/mg protein) with lower concentrations observed in the interpeduncular nucleus (220 fmol/mg protein), periaqueductal grey (180 fmol/mg protein), habenula (125 fmol/mg protein), ovary (18 fmol/mg protein) and testes (14 fmol/mg protein). The sensitivity of the GnRH-luciferin binding assay also permits one to detect low, yet significant concentrations of GnRH binding sites in the hypothalamus (4.5 fmol/mg protein) and posterior pituitary (13 fmol/mg protein).

EXAMPLE 3

A solution of 4.0 mg. of N-succinimidyl-2-(2-pyridyldithio) propionate (SPDP) in 1.0 cc. of absolute alcohol is mixed with 1.0 mg. of amino-derivatized firefly luciferin and incubated for 30 minutes at room temperature with constant shaking to form an SPDP-luciferin conjugate. The conjugate is then reduced by addition of dithiothreitol to provide a final concentration of 0.25M at pH 7.0 and held for 30 minutes at room temperature. The mixture is then placed in a Sephadex G-10 chromatographic column (80×1 cm.) and eluted with 100 mM sodium phosphate buffer.

A solution of 4.0 mg. of SPDP in absolute alcohol is mixed with 4.0 mg. of D-lys[6]-Gonadotropin releasing hormone (GnRH) and incubated with constant shaking for 30 minutes at room temperature to link the SPDP- to D-lys[6]-GnRH.

The reduced SPDP-luciferin solution and the SPDP-GnRH are then mixed in equal molar ratio in a phosphate buffer at pH 7.0 to link the luciferin and GnRH via thiol disulfide exchange.

The product has properties and uses comparable to the product of Example 2.

EXAMPLE 4

A nucleotide, monosuccinyl (adenosine 3':5'-cyclic mono-phosphate, (cAMP), is covalently linked to firefly luciferin using the procedure of Example 2 and the carbodiimide of Example 2. The resulting luciferin-monosuccinyl-cAMP conjugate is purified by high performance liquid chromatography.

The product is useful in bioluminescent immunoassay of cAMP.

EXAMPLE 5

A steroid, 17-hemisuccinyl-estradiol is covalently linked to firefly luciferin using the procedure and carbodiimide of Example 2. The resulting luciferin-17-hemisuccinyl-estradiol is purified by high performance liquid chromatography.

I claim:

1. A compound for use in bioluminescent assays comprising an amino terminated firefly luciferin derivative having bioluminescent activity, said amino terminated firefly luciferin derivative having the structure:

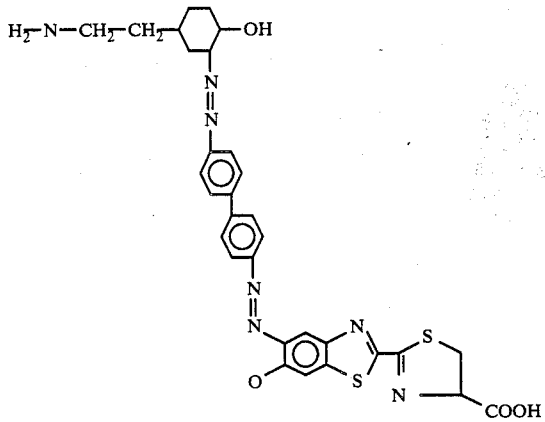

wherein said amino terminated firefly luciferin derivative is covalently linked to a biologically active compound, said linkage formed by condensation between (1) a reaction product of a biological active compound and N-succinimidyl-3(2-pyridyldithio) propionate and (2) the product of reacting said amino terminated derivative of firefly luciferin with N-succinimidyl-3(2-pyridyldithio) propionate and reducing the reaction product.

2. A compound for use in the bioluminescent immuno assays, ligand binding assays or ligand receptor assays comprising an amino terminated firefly luciferin, said amino terminated firefly luciferin having the structure:

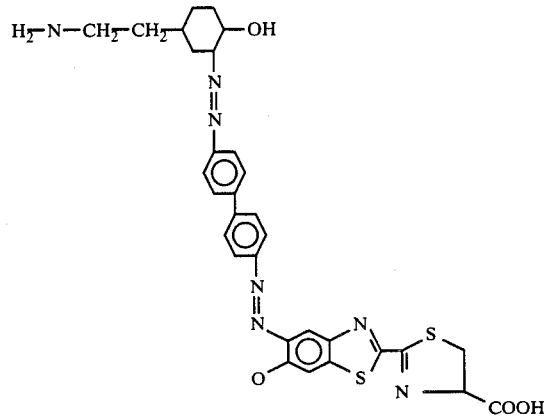

and said amino terminated firefly luciferin being covalently joined to a protein retaining its bioluminescent properties wherein said joining is by peptide linkage resulting from carbodiimide condensation of carboxyl groups on said protein and the amino group of said amino terminated firefly luciferin.

3. Immunoassay, ligand binding assay or ligand receptor binding method determining the concentration of a material having a biologically active group comprising mixing with a sample of said material an assay reagent in which an amino terminated firefly luciferin having the structure:

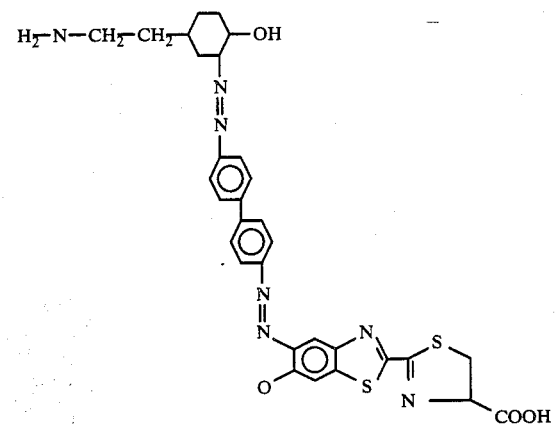

is covalently bonded by a peptide linkage to a compound having a group for biological combination with said material, said compound being selected from the group consisting of polypeptides and neurotransmitters; said amino terminated firefly luciferin being covalently bonded by carbodiimide condensation of carboxyl groups carried by said biologically active group and amino group of said amino-terminated firefly luciferin, incubating said mixture under controlled conditions of time, temperature, pH and concentration to bond said material to said reagent to the active groups of said material and said reagent, separating the product resulting from the bonding of said material and said reagent, reacting luciferase with said product to coact with the luciferin moiety to produce bioluminescent.

4. Immunoassay, ligand binding assay or ligand receptor binding method for determining the concentration of a material having a biologically active group comprising mixing with a sample of said material an assay reagent in which an amino-terminated firefly lucifering having the structure:

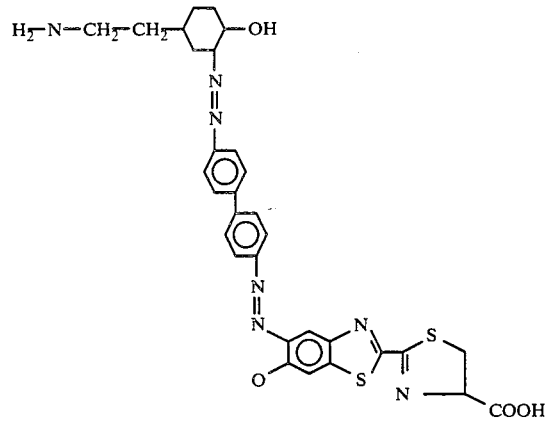

is covalently bonded by a disulfide linkage to a compound having a group for biological combination for said material; said compounds being selected from the group consisting of polypeptides and neurotransmitters, said disulfide linkage formed by condensation between (1) a reaction product of a biologically active compound and N-succinimidyl-3-(2-pyridyldithio) propionate and (2) the product of reacting an amine terminated derivative of firefly luciferin with N-succinimidyl-3-(2-pyridyldithio) propionate and reducing the reaction product, incubating said mixture under controlled conditions of time, temperature, pH and concentration to bond said material to said reagent through the active groups of said material and said reagent, separating the product resulting from the bonding of said material and said reagent, reacting luciferase with said product to coact with the luciferin moitey to produce bioluminescence.

* * * * *